United States Patent [19]

Morris

[11] Patent Number: 5,392,633

[45] Date of Patent: Feb. 28, 1995

[54] MEASURING THE STRENGTH OF ABRASIVE GRAINS

[75] Inventor: William G. Morris, Rexford, N.Y.

[73] Assignee: General Electric Company, Worthington, Ohio

[21] Appl. No.: 16,638

[22] Filed: Feb. 12, 1993

[51] Int. Cl.$^6$ .................. G01N 3/56; G01N 19/02; G01D 1/16

[52] U.S. Cl. ................................. 73/7; 73/790

[58] Field of Search ............ 73/790, 7, 78, 87, 818, 73/866, 821

[56] References Cited

U.S. PATENT DOCUMENTS

| | | | |
|---|---|---|---|
| 3,053,073 | 9/1962 | Baughman | 73/7 |
| 5,133,209 | 7/1992 | Noguchi et al. | 73/7 |

FOREIGN PATENT DOCUMENTS

| | | |
|---|---|---|
| 0361172 | 4/1990 | European Pat. Off. |
| 0447156 | 9/1991 | European Pat. Off. |
| 04890851 | 8/1993 | European Pat. Off. |
| 8621597 | 8/1986 | Germany |
| 60-017047 | 1/1985 | Japan |
| 1059478A | 12/1993 | U.S.S.R. |

OTHER PUBLICATIONS

Belling, N. G., and Bialy, L., "The Friatester–10 Years Later," *Industrial Diamond Review*, Aug. 1974, pp. 285–291.

Belling, N. G., "Friatesting & Diamond Strength: A Review," *Industrial Diamond Review*, Mar. 1992, pp. 133–137.

Brecker, J. N., "The Fracture Strength of Abrasive Grains," *Journal of Engineering for Industry*, Nov. 1974, pp. 1253–1257.

Field, J. E., "Strength and Fracture Properties of Diamond," in *The Properties of Diamond*, J. E. Field, ed., 1979 Academic Press, pp. 281–324.

Field, J. E., and Freeman, C. J., "Strength and Fracture Properties of Diamond," *Philosophical Magazine A*, vol. 43, No. 3, 1981, pp. 595–618.

Field, J. E., "Strength, Fracture and Erosion Properties of Diamond," in *The Properties of Natural and Synthetic Diamond*, J. E. Field, ed., 1992 Academic Press, pp. 473–513.

Himmel, T., et al., "Crushing Strength of Diamond Grits," *Journal of Hard Materials*, vol. 1, No. 2, 1990, pp. 103–121.

Stupkina, L. M., "Impact Strength of Diamond", *Soviet Physics–Crystallography*, vol. 15, No. 4, Jan.–Feb. 1971, pp. 728–730.

Primary Examiner—Richard E. Chilcot, Jr.
Assistant Examiner—William L. Oen

[57] ABSTRACT

An apparatus and method of speedily measuring the strength of individual abrasive grains such as diamonds in which the grains are crushed between two hard rollers and the compressive force exerted on the grain by the rollers at the moment of fracture is measured.

7 Claims, 1 Drawing Sheet

MEASURING THE STRENGTH OF ABRASIVE GRAINS

BACKGROUND OF THE INVENTION

The present invention relates to an apparatus and method for measuring the strength of individual abrasive grains.

It is known to measure the strength of a batch of grains by placing a small sample of the batch in a capsule with a steel ball, agitating it vigorously for a fixed amount of time, and measuring the amount of fragments produced. One disadvantage of this method is that it measures the strength of the weakest grains while giving little information about the strength of the strongest grains. Another disadvantage is that it has a low ability to discriminate among batches of similar hardness.

It is also known to measure the strength of individual grains by crushing them one at a time in a press. In this method individual grains are placed in a press between two anvils which move together along a single axis with increasing force until the grain fractures. One disadvantage of this method is that it takes one to two minutes to measure the strength of each grain. This method is avoided in commercial applications because of this lack of speed.

For the foregoing reasons, there is a need for a speedy means of measuring the strength of individual abrasive grains.

SUMMARY OF THE INVENTION

The present invention is directed to an apparatus and method that satisfies these needs. An apparatus having features of the present invention comprises a pair of hard counter-rotating rollers adapted with a means to measure the compressive force applied by the rollers to grains passing between the rollers at the moment of grain fracture.

A method according to the present invention comprises drawing a grain of hard material into a gap between two rollers and thus compressing the grain until it fractures, while measuring the peak compressive force necessary to fracture the grain.

It is an object of this invention to provide a speedy and accurate means of measuring the strength of individual grains of hard material.

BRIEF DESCRIPTION OF THE DRAWING

The above and other objects and advantages of the invention will be apparent upon consideration of the following detailed description, taken in conjunction with the accompanying drawings, in which like reference characters refer to like parts throughout, and in which.

DETAILED DESCRIPTION OF THE INVENTION

I. Theory of Operation

Figure 1:
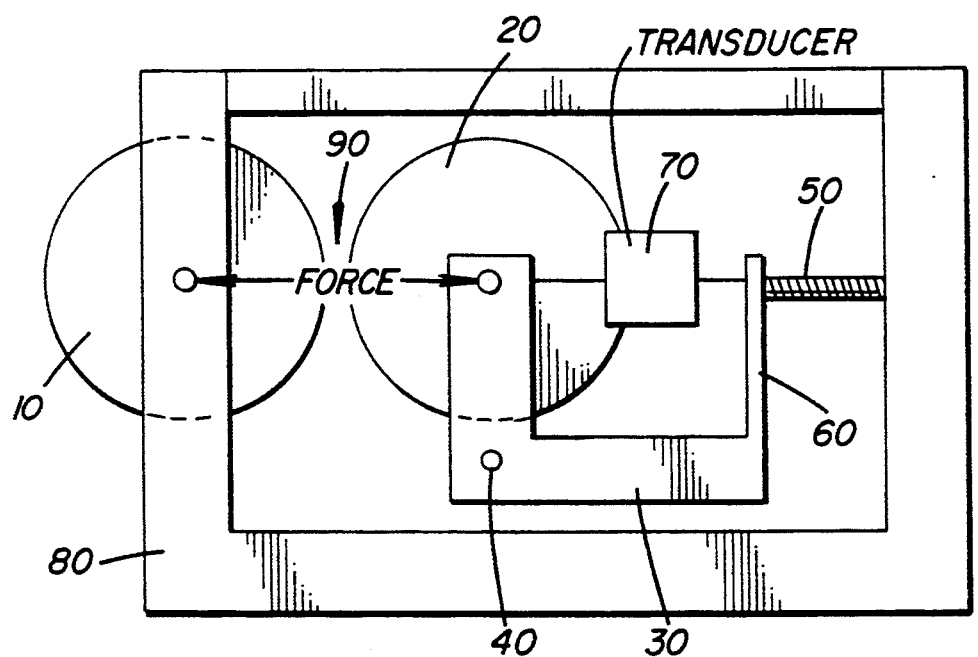
FIG. 1 is a representation of an embodiment of the present invention.

Individual abrasive grains are dropped into a narrow gap between two counter-rotating rollers constructed of a hard material. Because the size of the grain is greater than the gap, a compressive force is exerted on the grain as it is drawn into the gap by the frictional forces between it and the rollers. The compressive force exerted on the grain by the rollers is measured. At the point where the force reaches a level exceeding the strength of the grain it fractures. The peak compressive force is displayed or recorded.

II. Description of Preferred Embodiments

The rollers are preferably made of a material of hardness equal to or greater than 8 on the Mohs scale of hardness. In one preferred embodiment the rollers are made of tungsten carbide. Softer materials do not reliably break the hardest abrasive grains such as grains of diamond. Instead, the hardest grains will create indentations in softer rollers and fail to fracture.

FIG. 1 depicts a preferred embodiment of the invention. One roller 10 is rotatably fixed to a frame 80 and the second roller 20 is rotatably mounted on a beam 30 which is supported by a pivot 40 and a rigid, adjustable "gap adjust" member 50. The pivot 40 and gap adjust 50 are supported by frame 80. The gap adjust is threaded and may be turned to alter the size of the gap 90 between the rollers so as to accommodate various sizes of grains. At least a portion of the beam 60 possesses a degree of flexibility such that it may act as a spring. The motion of the second roller 20 in the direction of the gap 90 is measured by a suitable transducer 70 such as a linear voltage differential transformer. The output of the transducer 70 is an electrical signal which is proportional in voltage to the deflection of the second roller 20 and hence proportional to the compressive force exerted on the grain. The rollers are counter-rotated by any suitable drive mechanism.

In a preferred embodiment the transducer output is converted into a digital signal and stored or manipulated by a computer.

Data collected by the speedy application of the present invention is especially useful in providing feedback information for control of grain production processes and for grading batches of grains for use.

The strength of any hard grain may be measured by application of the present invention. Such grains include, but are not limited to, the following: diamond, cubic boron nitride, wurtzite system boron nitride, silicon carbide, aluminum oxide, garnet, and other materials used as abrasives.

The following example is illustrative:

Example

Using an apparatus conforming to the preferred embodiment as described above the hardness of 100 synthetic diamonds was measured. Diamonds were fed sequentially into the measuring apparatus. The time elapsed between the first measurement and the 100th measurement was a total of 7 minutes and 13 seconds. The data collected is reported in TABLE 1 in order of grain strength.

Thus it is seen that an apparatus and method for speedily measuring the strength of individual grains of hard materials is provided. One skilled in the art will appreciate that the present invention can be practiced by other than the preferred embodiments which are presented for purposes of illustration and not of limitation, and the present invention is limited only by the claims which follow.

TABLE 1

| No. | lbs. |
|---|---|
| 1 | 7.05 |
| 2 | 13.38 |
| 3 | 16.13 |
| 4 | 17.43 |
| 5 | 18.05 |
| 6 | 18.67 |
| 7 | 19.35 |

TABLE 1-continued

| No. | lbs. |
|---|---|
| 8 | 20.90 |
| 9 | 24.79 |
| 10 | 25.83 |
| 11 | 27.85 |
| 12 | 28.32 |
| 13 | 29.36 |
| 14 | 31.17 |
| 15 | 32.11 |
| 16 | 33.92 |
| 17 | 34.49 |
| 18 | 34.91 |
| 19 | 35.06 |
| 20 | 35.48 |
| 21 | 37.14 |
| 22 | 37.87 |
| 23 | 37.97 |
| 24 | 39.01 |
| 25 | 39.52 |
| 26 | 40.61 |
| 27 | 41.03 |
| 28 | 41.60 |
| 29 | 42.84 |
| 30 | 42.90 |
| 31 | 44.04 |
| 32 | 47.25 |
| 33 | 47.36 |
| 34 | 47.77 |
| 35 | 48.71 |
| 36 | 48.76 |
| 37 | 50.11 |
| 38 | 50.11 |
| 39 | 50.26 |
| 40 | 51.35 |
| 41 | 51.51 |
| 42 | 52.49 |
| 43 | 52.65 |
| 44 | 52.91 |
| 45 | 53.01 |
| 46 | 53.79 |
| 47 | 54.36 |
| 48 | 54.41 |
| 49 | 54.88 |
| 50 | 55.24 |
| 51 | 55.76 |
| 52 | 56.49 |
| 53 | 57.01 |
| 54 | 57.16 |
| 55 | 57.47 |
| 56 | 57.52 |
| 57 | 58.09 |
| 58 | 58.77 |
| 59 | 59.70 |
| 60 | 60.27 |
| 61 | 61.62 |
| 62 | 63.75 |
| 63 | 64.32 |
| 64 | 64.89 |
| 65 | 68.62 |
| 66 | 70.39 |
| 67 | 71.37 |
| 68 | 72.20 |
| 69 | 72.46 |
| 70 | 73.45 |
| 71 | 73.71 |
| 72 | 75.94 |
| 73 | 75.99 |
| 74 | 76.20 |
| 75 | 76.98 |
| 76 | 77.86 |
| 77 | 77.91 |
| 78 | 80.76 |
| 79 | 80.76 |
| 80 | 80.87 |
| 81 | 80.92 |
| 82 | 81.02 |
| 83 | 81.44 |
| 84 | 87.04 |
| 85 | 88.13 |
| 86 | 89.22 |
| 87 | 89.79 |
| 88 | 90.15 |
| 89 | 93.37 |
| 90 | 93.57 |
| 91 | 94.56 |
| 92 | 95.29 |
| 93 | 99.43 |
| 94 | 108.36 |
| 95 | 108.62 |
| 96 | 110.85 |
| 97 | 111.00 |
| 98 | 113.96 |
| 99 | 134.65 |
| 100 | 135.80 |

What is claimed is:

1. Apparatus for measuring the strength of abrasive grains, said apparatus comprising:
   a first hard roller;
   a second hard roller;
   a drive means for counter-rotating said first and second hard rollers;
   a compressing means for a exerting compressive force between said first and second hard rollers;
   a measuring means for measuring the compressive force exerted between said first and second hard rollers,
   said compressing means comprising:
   a frame to which said first hard roller is rotatably fixed;
   a beam to which said second hard roller is rotatably fixed, said beam comprising a flexible portion and said beam being mounted on said frame.

2. The apparatus of claim 1 wherein the measuring means is a transducer fixed between said beam and said frame such that it can be used to measure the lateral motion of said second hard roller relative to said first hard roller.

3. The apparatus of claim 2 wherein said beam is mounted on said frame by means of a pivot and a gap adjust member such that the distance between said first and second hard rollers may be varied by adjustment of said gap adjust member.

4. The apparatus of claim 3 wherein said measuring means additionally comprises a computer which converts an electrical output from said transducer into a digital signal.

5. Method of measuring the strength of abrasive grains, said method comprising:
   counter-rotating a first hard roller and a second hard roller;
   interposing an abrasive grain between said first and second hard rollers;
   compressing the grain by applying a compressive force by means of said first and second hard rollers until said abrasive grain fractures;
   measuring said compressive force;
   said first hard roller being rotatably mounted to a frame and said compressive force being applied by means of a beam comprising a flexible portion and mounted on said frame, said second hard roller being rotatably mounted to said beam.

6. The method of claim 5 wherein said measuring step comprises:
   measuring the deflection of said second hard roller in opposition to said compressive force;
   determining a maximum deflection at which said abrasive grain fractures;
   calculating from said maximum deflection a maximum force at which said abrasive grain fractures.

7. The method of claim 6 wherein said deflection of said second hard roller is measured by means of a transducer.

* * * * *